(12) United States Patent
Kodavanti et al.

(10) Patent No.: US 11,878,104 B2
(45) Date of Patent: Jan. 23, 2024

(54) WOUND DRESSING AND A WOUND THERAPY APPARATUS

(71) Applicant: CONVATEC LIMITED, Flintshire (GB)

(72) Inventors: Ankur Kodavanti, Banagalore (IN); Greeshma Girijakumari, Banagalore (IN); Harshad Kulkarni, Banagalore (IN); Joshin Sahadevan, Banagalore (IN); Praveen Kadni, Banagalore (IN); Sandeep Damodaran, Banagalore (IN); Srinivasan Jayaraman, Banagalore (IN)

(73) Assignee: ConvaTec limited, Flintshire (GB)

( * ) Notice: Subject to any disclaimer, the term of this patent is extended or adjusted under 35 U.S.C. 154(b) by 0 days.

(21) Appl. No.: 17/179,716

(22) Filed: Feb. 19, 2021

(65) Prior Publication Data

US 2021/0260258 A1    Aug. 26, 2021

Related U.S. Application Data

(63) Continuation of application No. PCT/GB2021/050419, filed on Feb. 19, 2021.

(30) Foreign Application Priority Data

Feb. 20, 2020    (GB) .................................... 2002339

(51) Int. Cl.
  *A61F 13/00*    (2006.01)
  *A61M 1/00*    (2006.01)
  *A61F 13/02*    (2006.01)

(52) U.S. Cl.
  CPC ......... *A61M 1/74* (2021.05); *A61F 13/00068* (2013.01); *A61F 13/0216* (2013.01);
  (Continued)

(58) Field of Classification Search
  CPC .......... A61M 1/90; A61M 1/96; A61M 1/962; A61M 1/966; A61M 1/74;
  (Continued)

(56) References Cited

U.S. PATENT DOCUMENTS 11,141,100 B2    10/2021    Schoess et al.
11,376,164 B2    7/2022    McNulty et al.
(Continued)

FOREIGN PATENT DOCUMENTS

CN        103179929 A        6/2013
EP        2941231 B1        7/2022
(Continued)

OTHER PUBLICATIONS

US 11,395,768 B2, 07/2022, Locke et al. (withdrawn)
(Continued)

*Primary Examiner* — Andrew J Mensh
(74) *Attorney, Agent, or Firm* — Taft Stettinius & Hollister LLP; Ryan O. White; Derek B. Lavender (57) ABSTRACT

A wound dressing for pressure gradient wound therapy. The wound dressing includes a dressing body and an adhesive layer. The adhesive layer provides an adhesive region for providing a seal between the wound dressing and the periphery of a wound site, in use. Sensors are provided associated with the adhesive region, the sensors being configured to monitor one or more conditions indicative of a hermeticity of the seal between the wound dressing and the periphery of the wound site.

21 Claims, 2 Drawing Sheets

(52) U.S. Cl.
CPC ..... *A61M 1/962* (2021.05); *A61M 2205/3306* (2013.01); *A61M 2205/3327* (2013.01); *A61M 2205/3331* (2013.01); *A61M 2205/3334* (2013.01); *A61M 2205/3368* (2013.01); *A61M 2205/581* (2013.01); *A61M 2205/583* (2013.01)

(58) Field of Classification Search
CPC ...... A61M 2205/583; A61M 2205/581; A61M 2205/3327; A61M 2205/3334; A61M 2205/3306; A61M 2205/3368; A61M 2205/3331; A61F 13/02; A61F 13/0216; A61F 13/00068; A61F 2013/00957
USPC ........................................................ 604/319
See application file for complete search history.

(56) References Cited

U.S. PATENT DOCUMENTS

| | | | |
|---|---|---|---|
| 11,395,874 B2 | 7/2022 | Manwaring et al. | |
| 11,400,202 B2 | 8/2022 | Locke et al. | |
| 11,413,389 B2 | 8/2022 | Locke et al. | |
| 11,419,768 B2 | 8/2022 | Cavanaugh et al. | |
| 11,432,967 B2 | 9/2022 | Locke et al. | |
| 11,439,741 B2 | 9/2022 | Hartwell | |
| 11,446,184 B2 | 9/2022 | Hu et al. | |
| 11,452,640 B2 | 9/2022 | Long et al. | |
| 11,452,809 B2 | 9/2022 | Long et al. | |
| 11,452,810 B2 | 9/2022 | Robinson et al. | |
| 11,471,333 B2 | 10/2022 | Greener | |
| 11,471,584 B2 | 10/2022 | Locke et al. | |
| 11,497,653 B2 | 11/2022 | Earl et al. | |
| 11,504,033 B2 | 11/2022 | Hicks et al. | |
| 2008/0275327 A1* | 11/2008 | Faarbaek | A61B 5/68335 600/382 |
| 2010/0087791 A1* | 4/2010 | Kelch | A61M 1/73 604/319 |
| 2012/0016322 A1* | 1/2012 | Coulthard | A61M 1/964 604/385.01 |
| 2012/0109034 A1* | 5/2012 | Locke | A61M 1/0023 602/42 |
| 2017/0246041 A1* | 8/2017 | Cumming | A61F 13/12 |
| 2018/0318475 A1* | 11/2018 | Thomson | A61M 1/73 |
| 2020/0078499 A1* | 3/2020 | Gadde | G16H 30/40 |
| 2021/0205140 A1 | 7/2021 | Hansen et al. | |
| 2021/0251565 A1 | 8/2021 | Hansen et al. | |
| 2021/0361491 A1 | 11/2021 | Hansen et al. | |
| 2021/0401359 A1 | 12/2021 | Schoess et al. | |
| 2022/0143297 A1 | 5/2022 | Gowans et al. | |
| 2022/0211932 A1 | 7/2022 | Robinson et al. | |
| 2022/0218528 A1 | 7/2022 | Askem et al. | |
| 2022/0218539 A1 | 7/2022 | Bradford et al. | |
| 2022/0218892 A1 | 7/2022 | Edwards et al. | |
| 2022/0226160 A1 | 7/2022 | Hartwell | |
| 2022/0226536 A1 | 7/2022 | Dagger et al. | |
| 2022/0233360 A1 | 7/2022 | Locke et al. | |
| 2022/0240841 A1 | 8/2022 | Drennan et al. | |
| 2022/0241113 A1 | 8/2022 | Hall et al. | |
| 2022/0241116 A1 | 8/2022 | Robinson et al. | |
| 2022/0241489 A1 | 8/2022 | Buan et al. | |
| 2022/0249291 A1 | 8/2022 | Derrick | |
| 2022/0249733 A1 | 8/2022 | Dagger et al. | |
| 2022/0249762 A1 | 8/2022 | Locke et al. | |
| 2022/0249763 A1 | 8/2022 | Asefi et al. | |
| 2022/0257422 A1 | 8/2022 | Lash et al. | |
| 2022/0257452 A1 | 8/2022 | Robinson et al. | |
| 2022/0257850 A1 | 8/2022 | Locke | |
| 2022/0273496 A1 | 9/2022 | Rehbein et al. | |
| 2022/0273498 A1 | 9/2022 | Andrews | |
| 2022/0273499 A1 | 9/2022 | Robinson et al. | |
| 2022/0280345 A1 | 9/2022 | Hartwell et al. | |
| 2022/0280713 A1 | 9/2022 | Collinson et al. | |
| 2022/0287884 A1 | 9/2022 | Kharkar | |
| 2022/0296426 A1 | 9/2022 | Wheldrake | |
| 2022/0296435 A1 | 9/2022 | Waite et al. | |
| 2022/0296770 A1 | 9/2022 | Cavanaugh et al. | |
| 2022/0313493 A1 | 10/2022 | Seddon | |
| 2022/0313494 A1 | 10/2022 | Lee | |
| 2022/0313893 A1 | 10/2022 | Hartwell et al. | |
| 2022/0331481 A1 | 10/2022 | Wheldrake | |
| 2022/0347017 A1 | 11/2022 | Robinson et al. | |
| 2022/0347018 A1 | 11/2022 | Collinson et al. | |
| 2022/0354701 A1 | 11/2022 | Kharkar et al. | |
| 2022/0354702 A1 | 11/2022 | Locke et al. | |
| 2022/0354703 A1 | 11/2022 | Lecoeuvre | |
| 2022/0354704 A1 | 11/2022 | Locke | |
| 2022/0355020 A1 | 11/2022 | Walton et al. | |
| 2022/0355021 A1 | 11/2022 | Locke | |
| 2022/0362060 A1 | 11/2022 | Rehbein et al. | |
| 2022/0362061 A1 | 11/2022 | Jeyakumaran et al. | |
| 2022/0362062 A1 | 11/2022 | Robinson et al. | |
| 2022/0370254 A1 | 11/2022 | Seddon et al. | |

FOREIGN PATENT DOCUMENTS

| | | | |
|---|---|---|---|
| EP | 3485922 B1 | 7/2022 | |
| EP | 3634338 B1 | 7/2022 | |
| EP | 3638172 B1 | 7/2022 | |
| EP | 4023197 A1 | 7/2022 | |
| EP | 2311509 B2 | 8/2022 | |
| EP | 3288510 B1 | 8/2022 | |
| EP | 3562520 B1 | 8/2022 | |
| EP | 3574877 B1 | 8/2022 | |
| EP | 3582731 B1 | 8/2022 | |
| EP | 4041155 A1 | 8/2022 | |
| EP | 4041161 A1 | 8/2022 | |
| EP | 2160166 B2 | 9/2022 | |
| EP | 2902068 B2 | 9/2022 | |
| EP | 4057960 A1 | 9/2022 | |
| EP | 2959933 B2 | 10/2022 | |
| EP | 3373874 B2 | 10/2022 | |
| EP | 3852829 B1 | 10/2022 | |
| EP | 4069169 A1 | 10/2022 | |
| EP | 4069170 A1 | 10/2022 | |
| EP | 4069171 A1 | 10/2022 | |
| EP | 4069172 A1 | 10/2022 | |
| EP | 4072488 A1 | 10/2022 | |
| EP | 4076310 A1 | 10/2022 | |
| EP | 3538165 B1 | 11/2022 | |
| EP | 4090393 A1 | 11/2022 | |
| WO | 2019020666 A1 | 1/2019 | |
| WO | 2019020666 A9 | 1/2019 | |
| WO | WO-2019030384 A2 * | 2/2019 | ........ A61F 13/00068 |

OTHER PUBLICATIONS

US 11,400,201 B2, 08/2022, Locke et al. (withdrawn)
International Search Report; European Patent Office; International Application No. PCT/GB2021/050419; dated May 18, 2021; 4 pages.
Written Opinion of the International Searching Authority; European Patent Office; International Application No. PCT/GB2021/050419; dated May 18, 2021; 7 pages.

* cited by examiner

WOUND DRESSING AND A WOUND THERAPY APPARATUS

CROSS-REFERENCE TO RELATED APPLICATIONS

This application is a continuation of International Application No. PCT/GB2021/050419 filed Feb. 19, 2021 and claims the priority of foreign Application No. GB2002339.6 filed Feb. 20, 2020. The disclosures of which are hereby incorporated herein in their entirety.

TECHNICAL FIELD OF THE INVENTION

The present invention relates to a wound dressing and a wound therapy apparatus, and in particular to a wound dressing for a pressure gradient wound therapy apparatus and an apparatus comprising the same.

BACKGROUND TO THE INVENTION

Pressure gradient wound therapy (positive or negative) is a known way of treating various wound types. Typically, this involves applying a pressure differential between a sealed region of a wound dressing and the surrounding environment to assist with healing the wound, e.g. through removal of oedema, increasing blood flow, mechanical contraction of the wound, increasing formation of granulation tissue and/or active removal of excess exudate from the wound. Wound therapy of this type is particularly effective for the treatment of open traumatic, non-traumatic and chronic wounds.

Such systems require a hermetic or near hermetic seal about the wound to perform adequately as any leak to or from the wound dressing makes it difficult to achieve the desired pressure level within the wound dressing. It is therefore important to ensure that this seal is present. In known systems, a pressure sensor may be used to determine the pressure level within the wound dressing, or perhaps the operating level of an associated source of negative pressure (e.g. a pump assembly) may be monitored to infer the presence of a leak from the wound dressing or the wound therapy apparatus as a whole. Such systems may be limited insofar as they may only indicate that the apparatus has a leak without any indication as to the location of that leak. Furthermore, some prior art systems may be unable to identify whether the leak is due to a reduced level of hermeticity between the wound dressing and the wound site or for some other reason (e.g. component malfunction).

There is therefore a need to provide means for monitoring the hermeticity of the seal about the wound site.

Also included in the Prior Art is WO2019/076967A2. This has sections describing NWPT systems; wound dressings; and wound dressings with sensors. Under the latter section, temperature sensors (e.g. thermistors), oxygen saturation or SPO2 sensors, optical (tissue colour) sensors, pH sensors and conductivity sensors are proposed. Notably the sensors are utilised in order to monitor characteristics of a wound as it heals.

It is an aim of an embodiment or embodiments of the invention to overcome or at least partially mitigate one or more problems with the prior art.

SUMMARY OF THE INVENTION

According to an aspect of the invention there is provided a wound dressing, optionally for pressure gradient wound therapy, the wound dressing comprising one or more sensors configured to monitor one or more conditions indicative of a hermeticity of the seal between the wound dressing and the periphery of the wound site.

The wound dressing may comprise an adhesive layer comprising an adhesive region for providing a seal between the wound dressing and the periphery of a wound site. The one or more sensors may be comprised in and/or associated with the adhesive region.

According to an aspect of the invention there is provided a wound dressing for pressure gradient wound therapy, the wound dressing comprising: an adhesive layer comprising an adhesive region for providing a seal between the wound dressing and the periphery of a wound site; wherein the adhesive layer comprises one or more sensors associated with the adhesive region, configured to monitor one or more conditions indicative of a hermeticity of the seal between the wound dressing and the periphery of the wound site.

Advantageously, providing one or more sensors in the dressing, preferably incorporated on, within or otherwise being associated with the adhesive region allows for the hermeticity of the seal between the wound dressing and the periphery of the wound site to be monitored directly, for example, without the need to infer the presence of a leak from measuring other parameters such as an operating level of a pump assembly associated with the wound dressing.

The wound dressing of the present invention may additionally allow for the location of an area of reduced hermeticity between the wound dressing and the periphery of the wound site (e.g. a specific region of the seal provided between the wound dressing and the user's skin by the adhesive region about the wound site) to be determined. Advantageously, the location of a leak from the wound dressing may be identified in contrast to prior art systems which may only be able to infer a leak in the wound dressing or wound therapy apparatus as a whole (and in complete contrast to the prior art wound dressings in which sensors monitor characteristics of a wound, rather than conditions indicative of a hermeticity of the seal between the wound dressing and the periphery of the wound site).

When used herein and throughout the specification the term "pressure gradient wound therapy apparatus" is intended to cover a wound therapy apparatus wherein a pressure differential (either positive or negative) is applied between a sealed region of the wound dressing and the surrounding environment.

As used herein, negative pressure wound therapy is a therapeutic technique using a suction dressing to remove excess exudation and promote healing in acute or chronic wounds. A vacuum of −50 to −200 mm Hg, or −75 to −150 mm Hg may be applied with typical negative pressure of −80 to −130 mm Hg, −100 to −130 mm Hg, or often about −125 mm Hg being applied to a wound.

For positive pressure wound therapy, a net positive pressure is applied to the wound, which may include providing simultaneous aspiration and irrigation of the wound. Positive pressure wound therapy may be carried out at a positive pressure of up to 50% atm., typically at a low positive pressure of up to 20% atm., more usually up to 10% atm. at the wound. Positive pressure wound therapy is known and referred to in US20180140755.

Optional features set out below may apply to any aspect of the invention.

In embodiments, the one or more sensors comprise a plurality of sensors, for example, at least 2, 4, 8, 16 or 24 sensors, arranged to monitor one or more conditions indicative of the hermeticity of the seal between the wound dressing and the periphery of the wound site in a plurality of regions of the wound dressing. The plurality of sensors may be arranged as a strip of sensors. For example, in some embodiments the plurality of sensors may be arranged in a strip which is configured to be provided about at least part of the wound site, in use. In some embodiments the plurality of sensors may be arranged in a strip configured to substantially surround the wound site, in use.

The sensor(s) may be provided about the wound site, in use, such that the one or more conditions monitored by the sensor(s) may be indicative of, and may be used to determine, a specific area or region of reduced hermeticity and hence a leak from that area or region of the wound dressing. For example, the sensor(s) may be provided such that the one or more conditions monitored by the sensor(s) are indicative of which half of a wound dressing is leaking; which quarter of the wound dressing is leaking; which eighth of the wound dressing is leaking; which sixteenth of the wound dressing is leaking; or which twenty-fourth of the wound dressing is leaking.

The provision of sensors capable of being used to determine the location of a leak at these higher levels of resolution, which can be occasioned by the provision of sufficient numbers of individual sensors, allows much greater precision in determining where a leak is occurring, and hence a more focused response, i.e. re-sticking the dressing in the particular region where it is leaking.

In some embodiments the one or more sensors are operable to output a signal indicative of the one or more monitored conditions for determining the hermeticity of the seal between the wound dressing and the periphery of the wound site. The one or more sensors may comprise an electrical output. The one or more sensors may be configured such that the signal indicative of the one or more monitored conditions may be output via either a wired or wireless connection with a controller, the controller being operable to determine the hermeticity of the seal between the wound dressing and the periphery of the wound site in dependence on the signal(s) received via such connection from the one or more sensors. The controller may be provided as part of the wound dressing, or may comprise a separate component of a wound therapy apparatus comprising the wound dressing. In embodiments the one or more sensors may be operable to output the signal to a remote device, such as a smartphone or the like, optionally via a controller.

The one or more sensors may be incorporated on, within or be otherwise associated with the adhesive region. For example, the one or more sensors may be embedded within the adhesive region. The adhesive region may comprise a channel or the like in which the one or more sensor may be located. In this way, the one or more sensors may be positioned within the adhesive region and sit "flush" with a surface of the adhesive region.

The one or more sensors may be configured to be positioned between the wound dressing and the periphery of the wound site, in use. The one or more sensors may be provided as a ring of sensors configured to be provided about the periphery of the wound site. The one or more sensors may be distributed within the adhesive region.

Preferably the sensors are provided only in the adhesive region, where they can monitor conditions indicative of a hermeticity of the seal, and not for example, in a dressing body, e.g. an absorbent dressing body.

The one or more sensors may be provided within a casing. In embodiments, each of the one or more sensors may be provided within a respective casing. The casing may comprise a plastics material. The casing may comprise a polymeric material. The casing may comprise a biocompatible material. In embodiments, the casing may comprise polyimide. The casing and/or the sensor(s) itself may comprise an adhesive portion for adhesively securing the casing/sensor(s) to the wound dressing and/or the user's skin, in use.

The one or more sensors may be electrically coupled to a power source. The power source may be provided integral with the wound dressing. Alternatively, the power source may be a separate component. The one or more sensors may alternatively comprise or be otherwise associated with one or more piezoelectric elements, and be powered through movement of the user whilst wearing the wound dressing.

In embodiments, the one or more sensors may comprise or may each comprise a micro-electromechanical system (MEMS) sensor. The one or more sensors may comprise or may each comprise a nano-electromechanical system (NEMS) sensor.

The one or more sensors may comprise a capacitive sensor. The or each capacitive sensor may comprise a moveable or deflectable sensing element capacitively coupled to an electrode. An increase or decrease in pressure may thereby be measured as a change in capacitance of the or each sensor due to movement/deflection of the sensing element under the applied pressure.

The one or more sensors may comprise a resistive sensor. The or each resistive sensor may comprise a moveable or deflectable sensing element. An increase or decrease in pressure may thereby be measured as a change in resistive values of one or more conductive elements of the resistive sensor(s) due to movement/distortion of the sensing element under the applied pressure.

The one or more sensors may comprise or may each comprise a pressure sensor. The one or more pressure sensors may be operable to obtain a measurement indicative of the pressure within the wound dressing. For example, the one or more sensors may be operable to obtain a measurement of an absolute pressure value within the wound dressing. The one or more sensors may be operable to obtain a relative pressure value within the wound dressing, which may be relative to atmospheric pressure or to a desired/optimum pressure value for the wound dressing, for example.

The one or more pressure sensors may be operable to obtain a measurement indicative of a pressure associated with the seal provided between the adhesive region and the periphery of the wound site. The pressure may comprise an average pressure value determined by two or more pressure sensors, which may change over time as a result of different use scenarios for the wound dressing (e.g. atmospheric change, a user wearing clothing over the dressing, etc.). A current pressure level as determined by one or more of the sensors may be comparable with the average pressure value to determine a leak. For example, a leak may be determined where a current measurement of the pressure level for a given pressure sensor differs from the average pressure value by a given amount, which may indicate a detaching of the adhesive seal at the corresponding location, for example.

In embodiments, the one or more pressure sensors may be operable to obtain a measurement of a rate of change of pressure associated with the wound dressing.

The one or more sensors may comprise or may each comprise a temperature sensor. The one or more temperature sensors may be operable to obtain a measurement indicative of the temperature associated with the wound dressing, e.g. the temperature within the wound dressing or a temperature associated with the seal between the adhesive region and the periphery of the wound site. In embodiments, the one or more sensors may be operable to obtain a measurement of a temperature gradient associated within the wound dressing. For example, in such embodiments the one or more sensors may be operable to obtain a measurement indicative of a temperature difference between two or more locations of the wound dressing, or between the wound dressing and the user's skin, e.g. the temperature of the user's skin at the periphery of the wound site. Here, a temperature gradient between two locations expected to be at the same temperature, or between the wound dressing and the user's skin may be indicative of a reduced hermeticity.

The one or more sensors may be operable to obtain a relative temperature value associated with the wound dressing. In embodiments, the relative temperature value may be calculated as an average temperature value determined by two or more temperature sensors, which may change over time as a result of different use scenarios for the wound dressing (e.g. atmospheric change, a user wearing clothing over the dressing, etc.). A current measurement of a temperature level may be comparable with the average temperature value to determine a leak. For example, a leak may be determined where a current measurement of the temperature level for a given temperature sensor differs from the average temperature value by a given amount. A leak may be determined upon measurement of a drop in temperature level for a given temperature sensor, as might be expected if the sensor becomes separated from the skin of the user which is likely to be at a higher temperature than the surrounding environment.

The one or more sensors may comprise or may each comprise an optical sensor. A light intensity level measured by the one or more optical sensors may be indicative of a level of hermeticity between the wound dressing and the periphery of the wound site. For example, an increased level of light intensity may be indicative of a separation of the adhesive region and the user's skin—i.e. a reduction in hermeticity. A change in the frequency content of light incident on one or more optical sensors may be indicative of a level of hermeticity between the wound dressing and the periphery of the wound site.

In embodiments, the one or more sensors may comprise or may each comprise an airflow sensor. The one or more airflow sensors may be operable to determine a measurement indicative of a speed and/or direction of airflow across the sensor(s). The one or more airflow sensors may be positioned within the wound dressing such that the speed and/or direction of airflow across the sensor(s) is indicative of an airflow to or from the wound site—i.e. a leak. The airflow speed may indicate a leak rate, for example.

The one or more sensors may comprise or may each comprise a contact sensor. The one or more contact sensors may comprise a first contact and a second contact. The first contact may be attached, embedded or otherwise coupled to the adhesive layer. The second contact may comprise an adhesive or the like for attaching the second contact to the skin of a user. In use, the relative positions of the first and second contacts may be indicative of the hermeticity of the seal between the wound dressing and the periphery of the wound side. For example, the contacts being proximal to each other or in direct contact with each other may be indicative of an acceptable seal at that location between the wound dressing and the user's skin. The contacts being separate from one another may indicate a region of reduced hermeticity. The one or more contact sensors may form a strain sensor. A monitored level of strain may be indicative of a level of hermeticity, for example, through measurement of a strain experienced through the first and second contacts being moved in different directions.

The one or more sensors may comprise or may each comprise an audio sensor. The one or more audio sensors may be operable to detect an audio signal indicative of the hermeticity of the seal between the wound dressing and the periphery of the wound site. For example, in embodiments the audio signal may be indicative of an airflow across the audio sensor, thereby indicating a leak to or from the wound dressing.

As set out above, the one or more sensors may comprise a plurality of sensors. The plurality of sensors may be of the same type, e.g. two or more temperature, pressure, optical or airflow sensors. In embodiments, the plurality of sensors may comprise two or more different sensor types, for example, at least one temperature sensor (or a plurality thereof) and at least one pressure sensor (or a plurality thereof).

In some embodiments the wound dressing comprises one or more indicators. The one or more indicators may be operable to provide an indication to a user of the condition of the wound dressing in dependence on the one or more conditions monitored by the one or more sensors. For example, the one or more indicators may be operable to provide an indication indicative of the hermeticity of the seal between the wound dressing and the periphery of the wound site. The one or more indicators may be operable to provide the indication in dependence on the one or more monitored conditions being indicative of a reduction in hermeticity between the wound dressing and the periphery of the wound site.

The one or more indicators may be configured to be positioned, in use, about the periphery of the wound site. For example, in embodiments the one or more indicators may be configured to provide an indication at or proximal to the location of an area of reduced hermeticity in dependence on the one or more conditions monitored by the sensor(s). The location may preferably correspond to a specific area or region of the seal provided between the wound dressing and the user's skin about the periphery of the wound site.

In embodiments, the one or more indicators comprise a plurality of indicators, for example, at least 2, 4, 8, 16 or 24 indicators, arranged to provide an indication at or proximal to the location of reduced hermeticity in one or more of a plurality of regions of the wound dressing (e.g. in one or more of at least 2, 4, 8, 16 or 24 locations, corresponding to one or more of the associated sensors). The plurality of indicators may be arranged as a strip of indicators. For example, in some embodiments the plurality of indicators may be arranged in a strip which is configured to be provided about at least part of wound site, in use. In some embodiments the plurality of indicators may be arranged in a strip configured to substantially surround the wound site, in use. In embodiments each sensor may be provided with one or more corresponding indicator, for example, two indicators, one either side of the respective sensor.

The indicator(s) may be operable to indicate which half of a wound dressing is leaking; the indicator(s) may be operable to indicate which quarter of the wound dressing is leaking; the indicator(s) may be operable to indicate which eighth of the wound dressing is leaking; the indicator(s) may be operable to indicate which sixteenth of the wound dressing is leaking; or the indicator(s) may be operable to indicate which twenty-fourth of the wound dressing is leaking.

The provision of indicators capable of indicating the location of a leak at these higher levels of resolution, in response, for example to the detection by one or more of sufficient numbers of individual sensors, allows much greater precision in indicating where a leak is occurring, and hence a more focused response, i.e. re-sticking the dressing in the particular region where it is leaking.

The one or more indicators may comprise a visual indicator, such as a light (e.g. an LED or a bulb). The one or more indicators may be operable to control whether the light is illuminated and/or the colour of the light in dependence on the one or more monitored conditions. For example, the one or more indicators may be operable to illuminate the light in response to a reduction of hermeticity between the wound dressing and the periphery of the wound site. The one or more indicators may be operable to switch the colour of the light (e.g. from green to red) in response to a reduction of hermeticity between the wound dressing and the periphery of the wound site.

The one or more indicators may comprise an audible indicator. For example, the one or more indicators may be operable to control the output of a warning alert or alarm in dependence on the one or more monitored conditions. For example, in embodiments the one or more indicators may be operable to output a warning alert or alarm in response to a reduction of hermeticity between the wound dressing and the periphery of the wound site.

The wound dressing may include a dressing body formed of an absorbent material which may be positioned in contact with a wound, in use. The dressing body may be configured to absorb exudate from the wound, aided by the action of a connected pump assembly. The dressing body may comprise an absorbent foam material, for example. The foam material may comprise a superabsorbent foam material. The dressing body may be formed of a hydrocolloid material which may gel in the presence of an exudate. The hydrocolloid material may comprise a layer or multiple layers of gelling fibres and absorbent materials. The outer surface of the dressing may be constructed of a thin film layer (e.g. a polyurethane) enabling moisture vapour to exit the dressing at an increased rate. This combination would allow the wound therapy apparatus to manage fluid without the need of a canister. This may be referred to as a "canister-less" or "canister-free" system. In a variant, the wound dressing may be operable to be fluidly connected to a canister into which exudate removed from the wound may be withdrawn. The adhesive layer may be provided about the periphery of the dressing body. In this way, the dressing may define an interior region of the wound dressing.

The wound dressing may have a thickness between 1 mm to 20 mm, or 2 mm to 10 mm, or 3 mm to 7 mm, for example. The wound dressing may be comprised of one or more layers including an outer cover layer, an absorbent layer, a gel-forming fibre, an adhesive layer, a wound contact layer, a distribution layer, and combinations thereof. The wound dressing may include one or more absorbent layer(s). The absorbent layer may be a foam or a superabsorbent. If foam is used, the foam may also act as a distribution layer. The wound dressing may comprise an outer cover layer and one or more absorbent layer(s) and a silicone gel wound contact layer. The wound dressing may comprise an outer cover layer and one or more absorbent layer(s) in combination with a gel-forming fibre. The gel-forming fibre typically is in direct contact with the wound, and thus no additional wound contact layer is required i.e., a silicone gel wound contact layer does not require a silicone gel layer.

Gel-forming fibres include hygroscopic fibres which upon the uptake of wound exudate become moist slippery or gelatinous. The gel forming fibres can be of the type which retain their structural integrity on absorption of exudate or can be of the type which lose their fibrous form and become an amorphous or structureless gel. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The gel forming fibres are preferably chemically modified cellulosic fibres in the form of a fabric and in particular carboxymethylated cellulose fibres as described in PCT WO00/01425 to Azko Nobel UK Ltd, and can be provided by a layer of gel forming fibres preferably located in a port of the cover layer or as a layer of fibres in a conduit of the wound dressing. When present in the conduit, the layer of fibres can also serve to keep the conduit open to the passage of fluid in the event that the conduit is kinked or otherwise restricted by being lain on or leaned on by the user. The carboxymethylated cellulosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method described in BS EN 13726-1 (2002) "Test methods for primary wound dressings", section 3.2 "Free swell absorptive capacity". Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hydroentangled and thus comprises a series of apertures on a microscopic scale.

Where present, the absorbent layer of the wound dressing is capable of absorbing exudate from the wound and allowing the passage of fluid through it. The absorbent layer can comprise any absorbent capable of absorbing exudate while allowing the passage of fluid through it, such as a foam, sponge or fibre-based material, preferably the absorbent layer is provided by gel forming fibres of the same type or of a different type as those discussed above. The gel-forming fibres are hygroscopic fibres which upon the uptake of wound exudate become moist slippery or gelatinous and thus reduce the tendency for the surrounding fibres to adhere to the wound. The gel forming fibres are preferably spun sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit and more preferably are lightly substituted so that the absorbency of the fibres is limited. The gel forming fibres preferably have an absorbency of at least 2 grams 0.9% saline solution per gram of fibre (as measured by the method described above) but less than 30 grams 0.9% saline solution per gram of fibre. The gel forming fibres are preferably carboxymethylated cellulose fibres as described in PCT WO00/01425 to Azko Nobel UK Ltd which describes lightly carboxymethylated cellulose fabrics. The gel forming fibres are preferably lightly carboxymethylated in order to reduce the tendency of the absorbent layer to gel block and block the pathway for fluid from the wound, e.g. through the absorbent layer, the port and to a distal end of the conduit.

Preferably the absorbent layer, where present, is provided with fenestrations to aid the application of negative pressure to the wound and maintain the pathway for fluid from the wound, through the absorbent layer. Typically, however, fenestrations are only provided in internal absorbent layers. External absorbent layers, including those in direct contact with the wound, generally do not have mechanically added fenestrations, however, they may include openings between the fibres.

Although the absorbent layer can be in direct contact with the wound, preferably the dressing comprises a wound contact layer, positioned between the wound and the absorbent layer. The wound contact layer may be capable of absorbing exudate from the wound and transmitting it to the absorbent layer. Like the absorbent layer, the wound contact layer may be capable of allowing the passage of fluid through it so that pressure (either positive or negative) may applied to the wound and the pathway for fluid/exudate from the wound to the distal end of the conduit may be maintained.

The wound contact layer may include gel-forming fibres (e.g. of the type discussed herein), or a silicone gel, for example.

Preferably the wound contact layer comprises gel-forming fibres. The gel-forming fibres may be the same or a similar type to those comprising the absorbent layer but the wound contact layer may be strengthened to increase its integrity and that of the dressing. For example, the wound contact layer may be of the type described in EP 1904011 and comprise gel-forming fibres in the form of a mat with lines of longitudinal stitching made of cellulose or nylon or polyolefin yarn to increase the integrity of the layer. Preferably the wound contact layer is porous to maintain the pathway for fluid/exudate from the wound to the distal end of the conduit.

An outer cover layer of the dressing is provided as a bacterial and viral barrier layer which preferably resists the ingress of liquid and air but allows moisture vapour transmission. In this way the outer cover layer enhances the overall fluid handling capacity of the dressing by allowing for the escape of moisture vapour through the cover while enabling the application of pressure (either positive or negative) to the wound. The outer cover layer is for instance a layer having a MVTR of at least 10,000 g m² per 24 hours or in the range of from 10,000 gm$^{-2}$ to 50,000 g m$^{-2}$ per 24 hours measured by the method described in BS EN 13726-2 2002 "Test methods for primary wound dressings Part 2 Moisture vapour transmission rate of permeable film dressings". The cover layer may be in the form of a film of polyurethane, for example Epurex 912 T/129 manufactured by Covestro or Inspire 2350 manufactured by Coveris or Medifilm 426 manufactured by Mylan.

The cover layer can be provided with a port for connection to the conduit. The port is preferably located in the cover layer and overlies the absorbent layer towards the periphery of the absorbent layer so that it is not directly in vertical alignment with the centre of the dressing (or the wound when in use). This assists in the spread of exudate across the full extent of the absorbent layer.

The conduit of the dressing is preferably a transparent passageway secured to the outside of the cover layer at the proximal end of the conduit so as to surround the port in the cover layer from above. The conduit of the dressing may comprise a connector, at its distal end, for connecting the dressing to a source of pressure (either positive or negative), for example a pump. Preferably the connector is a luer lock to facilitate secure connection to the pump and to maintain the pressure within the wound dressing while the pump is temporarily disconnected. The connector preferably comprises a one-way lock to assist in the maintenance of the applied pressure. To resist collapse, the conduit may comprise an internal cylinder of nylon fibres to maintain openness of the conduit to fluid.

The dressing may further comprise a distribution layer, e.g., a pressure distribution layer, located between the absorbent layer and the outer cover layer which is gas and liquid permeable and particularly moisture vapour permeable and serves to aid access of exudate to a greater area of the absorbent layer by allowing it to spread under the distribution layer. The distribution layer also serves to even out the negative pressure applied to the wound over the whole dressing. The distribution layer preferably distributes exudate and negative pressure over the dressing. In this way, uptake of exudate by the absorbent layer is maximised before the exudate leaves the absorbent layer and activates the indicator means and the transfer of negative pressure to the wound is optimised. The distribution layer is preferably a foam layer such as a polyester foam of the type XD4200AS manufactured by Caligen or another suitable reticulated foam.

The dressing may also comprise additional optional layers such as an adhesive layer for adhering the dressing to the skin surrounding the wound to form a fluid tight seal. The adhesive layer may be applied to the side of dressing closest to the wound and may be provided with perforations to assist transport of exudate and fluid through the dressing. The adhesive layer may also be applied to any of the other layers to provide an island configuration such as to the cover layer.

According to another aspect of the invention there is provided a pressure gradient wound therapy apparatus, comprising the wound dressing of any preceding aspect of the invention and a pump assembly for providing a source of positive or negative pressure to the wound dressing, in use.

In embodiments, the wound therapy apparatus comprises a negative pressure wound therapy apparatus. In other embodiments, the wound therapy apparatus comprises a positive pressure wound therapy apparatus.

In embodiments, the apparatus may comprise a canister and the wound dressing may be fluidly connected to the canister into which exudate removed from the wound may be withdrawn. In other embodiments, the wound dressing may be formed of a hydrocolloid material which may gel in the presence of an exudate. This may be referred to as a "canister-less" system.

The pump assembly may be fluidly connected to an interior region of the wound dressing, for introducing and/or removing gas from within the wound dressing to control the pressure therein.

The apparatus may comprise a controller. In such embodiments, the one or more sensors are operable to output a signal indicative of the one or more monitored conditions to the controller for determining the hermeticity of the seal between the wound dressing and the periphery of the wound site. The one or more sensors may comprise an electrical output. The controller may comprise an electrical input. The controller may be operable to determine the hermeticity of the seal between the wound dressing and the periphery of the wound site in response to a signal, or signals from the one or more sensors. The one or more sensors may be configured such that the signal indicative of the one or more monitored conditions may be output via either a wired or wireless connection with the controller, the controller being operable to determine the hermeticity of the seal between the wound dressing and the periphery of the wound site in dependence on the signal(s) received via such connection from the one or more sensors. The controller may be provided as part of the wound dressing or pump assembly, or may comprise a separate component of the wound therapy apparatus.

The apparatus may comprise a remote device, e.g. a smartphone or the like. The remote device may comprise a display for presenting information indicative of the one or more monitored conditions and/or the hermeticity of the seal between the wound dressing and the periphery of the wound site. The display may be operable to display a location of an area or region of reduced hermeticity of the seal between the wound dressing and the periphery of the wound site. The location may preferably correspond to a specific area or region of the seal provided between the wound dressing and the user's skin about the periphery of the wound site. For example, in some embodiments the display may be operable to present an image of the wound dressing. The image of the wound dressing may comprise indicia thereon corresponding to respective locations of the wound dressing. The remote device may be operable to highlight indicia within the wound dressing image corresponding to the location of an area or region of reduced hermeticity of the seal between the wound dressing and the periphery of the wound site. The wound dressing may comprise corresponding indicia thereon such that the wound dressing image may be correlated with the wound dressing itself.

In embodiments, display may be operable to display at least 2, 4, 8, 16 or 24 locations of areas or regions of reduced hermeticity in one or more of a plurality of regions of the wound dressing image (e.g. in one or more of at least 2, 4, 8, 16 or 24 locations, corresponding to one or more of the associated sensors of the wound dressing).

The display may be operable to indicate which half of a wound dressing is leaking; the display may be operable to indicate which quarter of the wound dressing is leaking; the display may be operable to indicate which eighth of the wound dressing is leaking; the display may be operable to indicate which sixteenth of the wound dressing is leaking; or the display may be operable to indicate which twenty-fourth of the wound dressing is leaking.

The remote device may be communicably coupled to the one or more sensors via a controller of the apparatus or may be communicably coupled directly to the one or more sensors, in which case it may comprise the controller. For example, in embodiments the one or more sensors are operable to output a signal indicative of the one or more monitored conditions via either a wired or wireless connection with the controller and/or the remote device, the controller or remote device being operable to determine the hermeticity of the seal between the wound dressing and the periphery of the wound site in dependence on the received signal(s).

The apparatus may comprise a power source (e.g. a battery) for powering one or more components of the apparatus. The apparatus may comprise a power source for powering the one or more sensors. The power source may be integrated with the wound dressing. Alternatively, the power source may comprise a separate component electrically coupled with the relevant components of the apparatus.

According to a further aspect of the invention there is provided a control system for controlling operation of a pressure gradient wound therapy apparatus according to any aspect described herein, the control system comprising one or more controllers, and being configured to: receive an input signal from at least one sensor of the wound dressing indicative of the monitored one or more conditions; and output a control signal for controlling operation of the pressure gradient wound therapy apparatus in dependence on the one or more conditions.

In embodiments, the one or more controllers collectively comprise: at least one electronic processor having an electrical input for receiving the input signal. The one or more controllers may collectively comprise at least one electronic memory device electrically coupled to the at least one electronic processor and having instructions stored therein. The at least one electronic processor may be configured to access the at least one memory device and execute the instructions thereon so as to generate the control signal for controlling the wound therapy apparatus in dependence on the one or more conditions.

The control system may be configured to receive an input signal from a plurality of sensors. In embodiments, the one or more sensors may comprise or may each comprise a micro-electromechanical system (MEMS) sensor. The one or more sensors may comprise or may each comprise a nano-electromechanical system (NEMS) sensor.

The one or more sensors may comprise a capacitive sensor. The or each capacitive sensor may comprise a moveable or deflectable sensing element capacitively coupled to an electrode. An increase or decrease in pressure may thereby be measured as a change in capacitance of the or each sensor due to movement/deflection of the sensing element under the applied pressure.

The one or more sensors may comprise a resistive sensor. The or each resistive sensor may comprise a moveable or deflectable sensing element. An increase or decrease in pressure may thereby be measured as a change in resistive values of one or more conductive elements of the resistive sensor(s) due to movement/distortion of the sensing element under the applied pressure.

The control system may be configured to determine a hermeticity of the seal between the wound dressing and the periphery of the wound site in dependence on the one or more conditions.

The one or more conditions may comprise a pressure level. The one or more conditions may comprise a pressure level within the wound dressing. In such embodiments the control system may be configured to receive an input signal indicative of a measurement of an absolute pressure value within the wound dressing. The control system may be configured to receive an input signal indicative of a relative pressure value within the wound dressing, which may be relative to atmospheric pressure or to a desired/optimum pressure value for the wound dressing, for example.

The one or more conditions may comprise a pressure level associated with the seal provided between the adhesive region and the periphery of the wound site. The control system may be configured to calculate an average pressure value determined by two or more pressure sensors, which may change over time as a result of different use scenarios for the wound dressing (e.g. atmospheric change, a user wearing clothing over the dressing, etc.). The control system may be configured to compare a current measurement of a pressure level (e.g. from one or more pressure sensors) with the average pressure value and determine a leak in dependence thereon. For example, the control system may be operable to determine a leak in dependence on a current measurement of the pressure level for a given pressure sensor differing from the average pressure value by a given amount.

The control system may be configured to determine a pressure gradient associated with the wound dressing, for instance, between two or more locations of the wound dressing. In such embodiments, a pressure gradient between two locations expected to be at approximately the same pressure level may be indicative of a reduced hermeticity.

The one or more conditions may comprise a temperature. The one or more conditions may comprise a temperature associated with the wound dressing, e.g. the temperature within the wound dressing or a temperature associated with the seal between the adhesive region and the periphery of the wound site. In embodiments, the control system may be configured to determine temperature gradient associated within the wound dressing. For example, in such embodiments the control system may be configured to determine temperature difference between two or more locations of the wound dressing, or between the wound dressing and the user's skin, e.g. the temperature of the user's skin at the periphery of the wound site. Here, a temperature gradient between two locations expected to be at the same temperature, or between the wound dressing and the user's skin may be indicative of a reduced hermeticity.

The control system may be operable to obtain a measurement of a relative temperature value associated with the wound dressing. For example, the control system may be operable to calculate a relative temperature value as an average temperature value determined by two or more temperature sensors, which may change over time as a result of different use scenarios for the wound dressing (e.g. atmospheric change, a user wearing clothing over the dressing, etc.). The control system may be configured to compare a current measurement of a temperature level with the average temperature value and determine a leak in dependence thereon. For example, the control system may be operable to determine a leak in dependence on a current measurement of the temperature level for a given temperature sensor differing from the average temperature value by a given amount. The control system may be operable to determine a leak in dependence on a determination of a drop in temperature level for a given temperature sensor, as might be expected if the sensor becomes separated from the skin of the user which is likely to be at a higher temperature than the surrounding environment.

The one or more conditions may comprise a light level. For example, in some embodiments a light intensity level may be indicative of a level of hermeticity between the wound dressing and the periphery of the wound site. For example, an increased level of light intensity may be indicative of a separation of the adhesive region and the user's skin—i.e. a reduction in hermeticity. In such embodiments, the control system may be configured to receive an input signal indicative of a light intensity level associated with the wound dressing. The control system may be operable to determine a frequency content of light incident on one or more optical sensors associated with the wound dressing. A change in the frequency content of light incident on one or more optical sensors may be indicative of a level of hermeticity between the wound dressing and the periphery of the wound site.

The one or more conditions may comprise an airflow, for example the direction and/or speed of an airflow associated with the wound dressing. The control system may be configured to receive an input signal indicative of a direction and/or speed of an airflow associated within the wound dressing, e.g. to or from the wound dressing.

The control system may be configured to output a control signal for controlling operation of one or more indicators in dependence on the one or more conditions for providing an indication to a user of the wound dressing indicative of the hermeticity of the seal between the wound dressing and the periphery of the wound site. For example, the control system may be configured to output a control signal for controlling an indicator to provide an indication in dependence on the one or more monitored conditions being indicative of a reduction in hermeticity between the wound dressing and the periphery of the wound site. The control system may be operable to output a control signal to one or more indicators provided at or proximal to the location of an area of reduced hermeticity, for example, to direct a user to the location of an area or region of reduced hermeticity between the wound dressing and the periphery of the wound site. The location may preferably correspond to a specific area or region of the seal provided between the wound dressing and the user's skin about the periphery of the wound site.

In embodiments, the one or more indicators comprise a plurality of indicators, for example, at least 2, 4, 8, 16 or 24 indicators, arranged to provide an indication at or proximal to the location of reduced hermeticity in one or more of a plurality of regions of the wound dressing (e.g. in one or more of at least 2, 4, 8, 16 or 24 locations, corresponding to one or more of the associated sensors). The plurality of indicators may be arranged as a strip of indicators. For example, in some embodiments the plurality of indicators may be arranged in a strip which is configured to be provided about at least part of wound site, in use. In some embodiments the plurality of indicators may be arranged in a strip configured to substantially surround the wound site, in use. In embodiments each sensor may be provided with one or more corresponding indicator, for example, two indicators, one either side of the respective sensor.

The control system may be operable to output a control signal for controlling operation of the indicator(s) to indicate which half of a wound dressing is leaking; which quarter of the wound dressing is leaking; which eighth of the wound dressing is leaking; which sixteenth of the wound dressing is leaking; or which twenty-fourth of the wound dressing is leaking, for example.

In this way, the control system may be capable of indicating the location of a leak at these higher levels of resolution, in response, for example to the detection by one or more of sufficient numbers of individual sensors, allowing for a much greater precision in indicating where a leak is occurring, and hence a more focused response, i.e. re-sticking the dressing in the particular region where it is leaking.

In embodiments, the control system may be configured to output a control signal to a remote device. The control signal may be indicative of the one or more conditions indicative of the hermeticity of the seal between the wound dressing and the periphery of the wound site. The control signal may be output to the remote device for informing a user of the location of an area or region of reduced hermeticity between the wound dressing and the periphery of the wound site. Again, the location may preferably correspond to a specific area or region of the seal provided between the wound dressing and the user's skin about the periphery of the wound site.

The one or more indicators may comprise a visual indicator, such as a light. The control signal may be configured to control whether the light is illuminated and/or the colour of the light in dependence on the one or more monitored conditions. The control system may be configured to illuminate the light in response to a reduction of hermeticity between the wound dressing and the periphery of the wound site. The control system may be configured to switch the colour of the light (e.g. from green to red) in response to a reduction of hermeticity between the wound dressing and the periphery of the wound site.

The one or more indicators may be operable to provide an audible indicator. For example, the control system may be configured to control the output of a warning alert or alarm in dependence on the one or more monitored conditions. The control system may be configured to control the output of a warning alert or alarm in response to a reduction of hermeticity between the wound dressing and the periphery of the wound site.

The control system may be configured to control an operating level of a component of the wound therapy apparatus in dependence on the one or more monitored conditions. The component may comprise a pump assembly of the wound therapy apparatus. In such embodiments, the operating level may comprise a power output or motor speed of the pump assembly, for example. In some embodiments the control system may be configured to output a control signal for activating the pump assembly in response to the one or more monitored conditions being indicative of a reduced hermeticity between the wound dressing and the periphery of the wound site. The control system may be operable to output a control signal to increase the power output and/or motor speed of the pump assembly in response to a reduced hermeticity between the wound dressing and the periphery of the wound site. Advantageously, where the reduced hermeticity results in a leak to or from the wound dressing, the pump assembly may be controlled in response thereto to maintain a desired pressure level within the wound dressing.

In further embodiments, the control system may be operable to output a control signal for disabling operation of the pump assembly in response to the one or more monitored conditions being indicative of a reduced hermeticity between the wound dressing and the periphery of the wound site. For instance, in some cases the reduction in hermeticity (and resultant leak to or from the wound dressing) may be such that the pump assembly cannot act to reach the desired pressure level within the wound dressing, or in doing so would result in excessive energy consumption or wear on components of the pump assembly. Accordingly, it may be advantageous in such instances to cease operation of the pump assembly to prevent excess energy consumption and/or damage to the pump assembly.

According to a further aspect of the invention there is provided a method of controlling operation of the pressure gradient wound therapy apparatus according to any aspect described herein, the method comprising: obtaining a measurement of one or more conditions indicative of a hermeticity of the seal between the wound dressing and the periphery of the wound site using the one or more sensors; and controlling operation of the pressure gradient wound therapy apparatus in dependence on the one or more conditions.

The method may comprise obtaining a measurement of the one or more conditions using a plurality of sensors. In embodiments, the one or more sensors may comprise or may each comprise a micro-electromechanical system (MEMS) sensor. The one or more sensors may comprise or may each comprise a nano-electromechanical system (NEMS) sensor.

The method may comprise determining a hermeticity of the seal between the wound dressing and the periphery of the wound site in dependence on the one or more conditions.

The method may comprise outputting a signal indicative of the one or more monitored conditions for determining the hermeticity of the seal between the wound dressing and the periphery of the wound site. The signal indicative of the one or more monitored conditions may be output via either a wired or wireless connection with a controller. The method may comprise using the controller to determine the hermeticity of the seal between the wound dressing and the periphery of the wound site in dependence on the signal(s) received via such connection from the one or more sensors.

The one or more conditions may comprise a pressure level. The one or more conditions may comprise a pressure level within the wound dressing. For example, the method may comprise obtaining a measurement of an absolute pressure value within the wound dressing. The method may comprise obtaining a relative pressure value within the wound dressing, which may be relative to atmospheric pressure or to a desired/optimum pressure value for the wound dressing, for example.

The one or more conditions may comprise a pressure level associated with the seal provided between the adhesive region and the periphery of the wound site. The method may comprise calculating an average pressure value determined by two or more pressure sensors, which may change over time as a result of different use scenarios for the wound dressing (e.g. atmospheric change, a user wearing clothing over the dressing, etc.). The method may comprise comparing a current measurement of a pressure level (e.g. from one or more pressure sensors) with the average pressure value and determine a leak in dependence thereon. For example, the method may comprise determining a leak in dependence on a current measurement of the pressure level for a given pressure sensor differing from the average pressure value by a given amount.

The method may comprise obtaining a measurement of a pressure gradient associated with the wound dressing, for instance, between two or more locations of the wound dressing. In such embodiments, a pressure gradient between two locations expected to be at approximately the same pressure level may be indicative of a reduced hermeticity.

The one or more conditions may comprise a temperature. The one or more conditions may comprise a temperature associated with the wound dressing, e.g. the temperature within the wound dressing or a temperature associated with the seal between the adhesive region and the periphery of the wound site. In embodiments, the method may comprise obtaining a measurement of a temperature gradient associated within the wound dressing. For example, in such embodiments the method may comprise obtaining a measurement indicative of a temperature difference between two or more locations of the wound dressing, or between the wound dressing and the user's skin, e.g. the temperature of the user's skin at the periphery of the wound site. Here, a temperature gradient between two locations expected to be at the same temperature, or between the wound dressing and the user's skin may be indicative of a reduced hermeticity.

The method may comprise obtaining a measurement of a relative temperature value associated with the wound dressing. For example, the method may comprise calculating a relative temperature value as an average temperature value determined by two or more temperature sensors, which may change over time as a result of different use scenarios for the wound dressing (e.g. atmospheric change, a user wearing clothing over the dressing, etc.). The method may comprise comparing a current measurement of a temperature level with the average temperature value and determine a leak in dependence thereon. For example, the method may comprise determining a leak in dependence on a current measurement of the temperature level for a given temperature sensor differing from the average temperature value by a given amount. The method may comprise determining a leak in dependence on a determination of a drop in temperature level for a given temperature sensor, as might be expected if the sensor becomes separated from the skin of the user which is likely to be at a higher temperature than the surrounding environment.

The one or more conditions may comprise a light level. For example, in some embodiments a light intensity level may be indicative of a level of hermeticity between the wound dressing and the periphery of the wound site. For example, an increased level of light intensity may be indicative of a separation of the adhesive region and the user's skin—i.e. a reduction in hermeticity. In such embodiments, the method may comprise obtaining a measurement of a light intensity level associated with the wound dressing. The method may comprise determining a frequency content of light incident on one or more optical sensors associated with the wound dressing. A change in the frequency content of light incident on one or more optical sensors may be indicative of a level of hermeticity between the wound dressing and the periphery of the wound site.

The one or more conditions may comprise an airflow, for example the direction and/or speed of an airflow associated with the wound dressing. The method may comprise obtaining a measurement of a direction and/or speed of an airflow associated within the wound dressing, e.g. to or from the wound dressing.

The method may comprise outputting an indication to a user of the wound dressing in dependence on the one or more conditions monitored by the one or more sensors. For example, the method may comprise outputting an indication indicative of the hermeticity of the seal between the wound dressing and the periphery of the wound site. The method may comprise providing the indication in dependence on the one or more monitored conditions being indicative of a reduction in hermeticity between the wound dressing and the periphery of the wound site. The method may comprise providing an indication at or proximal to the location of an area of reduced hermeticity in dependence on the one or more monitored conditions, for example, to direct a user to the location of an area or region of reduced hermeticity between the wound dressing and the periphery of the wound site. The location may preferably correspond to a specific area or region of the seal provided between the wound dressing and the user's skin about the periphery of the wound site.

The method may comprise outputting an indication at a plurality of locations, for example, at least 2, 4, 8, 16 or 24 locations at or proximal to a location of reduced hermeticity (e.g. in one or more of at least 2, 4, 8, 16 or 24 locations, corresponding to one or more of the associated sensors).

The method may comprise outputting an indication to indicate which half of a wound dressing is leaking; which quarter of the wound dressing is leaking; which eighth of the wound dressing is leaking; which sixteenth of the wound dressing is leaking; or which twenty-fourth of the wound dressing is leaking, for example.

In this way, the method may include indicating the location of a leak at these higher levels of resolution, in response, for example to the detection by one or more of sufficient numbers of individual sensors, allowing for a much greater precision in indicating where a leak is occurring, and hence a more focused response, i.e. re-sticking the dressing in the particular region where it is leaking.

In embodiments, the method may comprise outputting a control signal to a remote device. The control signal may be indicative of the one or more conditions indicative of the hermeticity of the seal between the wound dressing and the periphery of the wound site. The control signal may be output to the remote device for informing a user of the location of an area or region of reduced hermeticity between the wound dressing and the periphery of the wound site. Again, the location may preferably correspond to a specific area or region of the seal provided between the wound dressing and the user's skin about the periphery of the wound site.

The method may comprise outputting a visual indicator, such as a light. The method may comprise controlling whether the light is illuminated and/or the colour of the light in dependence on the one or more monitored conditions. The method may comprise illuminating the light in response to a reduction of hermeticity between the wound dressing and the periphery of the wound site. The method may comprise switching the colour of the light (e.g. from green to red) in response to a reduction of hermeticity between the wound dressing and the periphery of the wound site.

The method may comprise outputting an audible indication. For example, the method may comprise controlling the output of a warning alert or alarm in dependence on the one or more monitored conditions. The method may comprise outputting a warning alert or alarm in response to a reduction of hermeticity between the wound dressing and the periphery of the wound site.

The method may comprise controlling an operating level of a component of the wound therapy apparatus in dependence on the one or more monitored conditions. The component may comprise a pump assembly of the wound therapy apparatus. In such embodiments, the operating level may comprise a power output or motor speed of the pump assembly, for example. In some embodiments the method may comprise activating the pump assembly in response to one or more monitored conditions being indicative of a reduced hermeticity between the wound dressing and the periphery of the wound site. The method may comprise increasing the power output/motor speed of the pump assembly in response to a reduced hermeticity between the wound dressing and the periphery of the wound site. Advantageously, where the reduced hermeticity results in a leak to or from the wound dressing, the pump assembly may be controlled in response thereto to maintain a desired pressure level within the wound dressing.

In further embodiments, the method may comprise disabling operation of the pump assembly in response to the one or more monitored conditions being indicative of a reduced hermeticity between the wound dressing and the periphery of the wound site. For instance, in some cases the reduction in hermeticity (and resultant leak to or from the wound dressing) may be such that the pump assembly cannot act to reach the desired pressure level within the wound dressing, or in doing so would result in excessive energy consumption or wear on components of the pump assembly. Accordingly, it may be advantageous in such instances to cease operation of the pump assembly to prevent excess energy consumption and/or damage to the pump assembly.

According to an aspect of the invention there is provided computer software which, when executed by one or more processors, causes performance of a method in accordance with a preceding aspect of the invention.

According to an aspect of the invention there is provided a computer readable medium comprising the computer software of a preceding aspect of the invention. Optionally, the computer readable medium comprises a non-transitory computer readable medium.

DESCRIPTION OF THE DRAWINGS

In order that the invention may be more clearly understood one or more embodiments thereof will now be described, by way of example only, with reference to the accompanying drawings, of which.

DETAILED DESCRIPTION

Embodiments disclosed herein relate to apparatus and methods of treating a wound with reduced or positive pressure (typically negative pressure), including pump and wound dressing components and devices. The devices and components may include a wound overlay and packing materials, which may be collectively referred to interchangeably herein as "dressings" or "wound dressings".

As disclosed herein the present invention may comprise an apparatus for providing pressure gradient wound therapy to a wound, comprising: the technology disclosed herein, a wound dressing described herein; and a source of positive or negative pressure.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds (either as a result of surgery, trauma, stemiotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

The technology disclosed can be used on an acute or chronic wound.

Wounds are believed to be more susceptible to infection under the following circumstances. If the wounds are chronic wounds, or if an object which caused the wound was dirty or contained bacteria, or from a bite, or contains remnant or a whole object that caused the wound, or a wound that is large or deep, or jagged edges to the wound, or elderly, or chronic because by their nature a wound site is open; and/or if the patient has: diabetes type 1 or type 2, is elderly, or has a compromised immune system.

Pressure gradient wound therapy may also be useful for treating second- and third-degree burns, as well as being useful for laparotomy surgery i.e., a large incision through an abdominal wall to gain access into the abdominal cavity.

In general, the invention relates to a wound dressing 10 for pressure gradient wound therapy, e.g. negative pressure wound therapy. The wound dressing 10 includes an adhesive layer 14 having an adhesive region for providing a seal between the wound dressing 10 and the periphery of a wound site, in use. The wound dressing 10 is configured such that the hermeticity of the seal between the wound dressing and the periphery of a wound site may be monitored, in use. The invention extends to a control system 50 and wound therapy apparatus 100 for pressure gradient wound therapy, along with a method 200 of controlling operation of a pressure gradient wound therapy apparatus.

Figure 1:
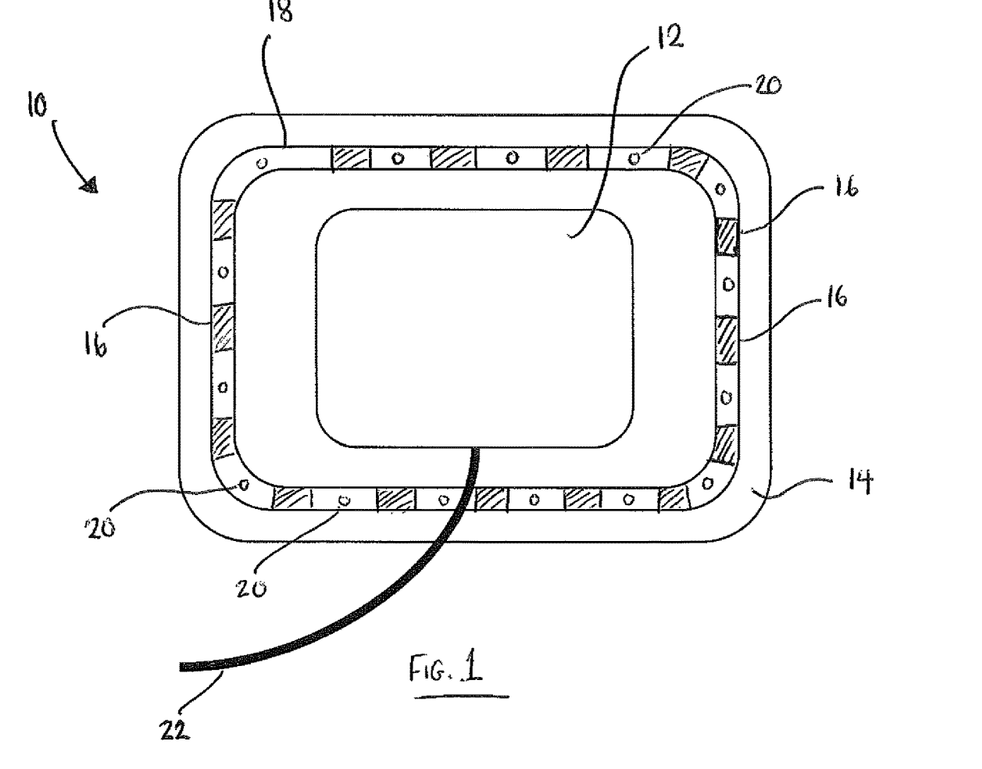
FIG. 1 is a schematic representation of an embodiment of a wound dressing.

FIG. 1 illustrates an embodiment of a wound dressing 10 in accordance with the invention.

The wound dressing 10 includes a dressing body 12 and an adhesive layer 14 provided about the periphery of the dressing body 12. A plurality of sensors 16 are provided within a strip 18 associated with the adhesive layer 14. The plurality of sensors 16 are configured, in use, to monitor one or more conditions indicative of a hermeticity of a seal between a wound dressing 10, and specifically the adhesive region of the adhesive layer 14, and the periphery of a wound site. A conduit 22 is provided for fluidly connecting the wound dressing 10 to a source of pressure (positive or negative) to control the pressure within the wound dressing 10.

The dressing body 12 comprises an absorbent material which is positioned in contact with a wound, in use. The dressing body 12 is configured to absorb exudate from the wound, aided by the action of an associated pump assembly 102 (FIG. 3) creating a pressure differential between the interior of the wound dressing 10 and the surrounding environment. Here, the exudate is retained within the dressing body 12. Specifically, the dressing body 12 is formed of a hydrocolloid material which gels in the presence of exudate. This may be referred to as a "canister-less" system. In a variant, exudate removed from the wound may instead be withdrawn into an accompanying canister rather than being retained within the dressing body 12 itself. The purpose of the adhesive layer 14, and specifically an adhesive region of the adhesive layer 14, is to provide a hermetic (or near hermetic) seal between the dressing 10 and the user's skin, in use, surrounding the dressing body 12 to define an interior region of the wound dressing 10 about the wound.

The plurality of sensors 16 comprise MEMS sensors and are provided embedded within the adhesive layer 14, arranged in a strip provided about the periphery of the dressing body 12. In the illustrated embodiment, the plurality of sensors 16 are pressure sensors 16 operable to obtain a measurement indicative of a pressure associated with the seal between the adhesive region and the periphery of the wound site. Specifically, the pressure sensors 16 comprise capacitive sensors having moveable sensing elements capacitively coupled and moveable with respect to an electrode. Upon the application of a pressure to the sensing element, e.g. due to the adhesive bond between the adhesive region and the user's skin during normal use, a certain pressure level is registered by the sensors 16 corresponding to an associated separation of the sensing element and electrode. If the seal become detached at or proximal to a given sensor 16, the pressure applied to the sensor 16 will drop as the force applied to the moveable sensing element due to the bond is removed. In turn, the sensing element of the sensor 16 moves with respect to the electrode (typically away from the electrode) and this is registered as a drop in pressure by the sensor 16, interpreted as a reduction in hermeticity at that location.

The strip 18 of sensors 16 additionally includes indicators in the form of LEDs 20. In use, the LEDs 20 can be illuminated in dependence on the condition(s) monitored by the sensors 16. Specifically, the LEDs 20 are provided about the periphery of the wound site in the same way as the sensors 16 in an alternating arrangement of LED 20, sensor 16, LED 20, sensor 16 . . . etc. The LEDs 20 are configured to provide an indication at or proximal to the location of an area of reduced hermeticity—i.e. a specific area or region of the seal provided between the wound dressing 10 and the user's skin about the periphery of the wound site, as determined using the sensors 16. For instance, each of the LEDs 20 are associated with an adjacent sensor 16 such that upon detection of a reduced hermeticity by a given sensor, the corresponding LED(s) may be used to indicate this to a user of the wound dressing 10 (or if more than one sensor 16 detects a reduced hermeticity, the LEDs 20 adjacent each such sensor are illuminated).

Figure 2:
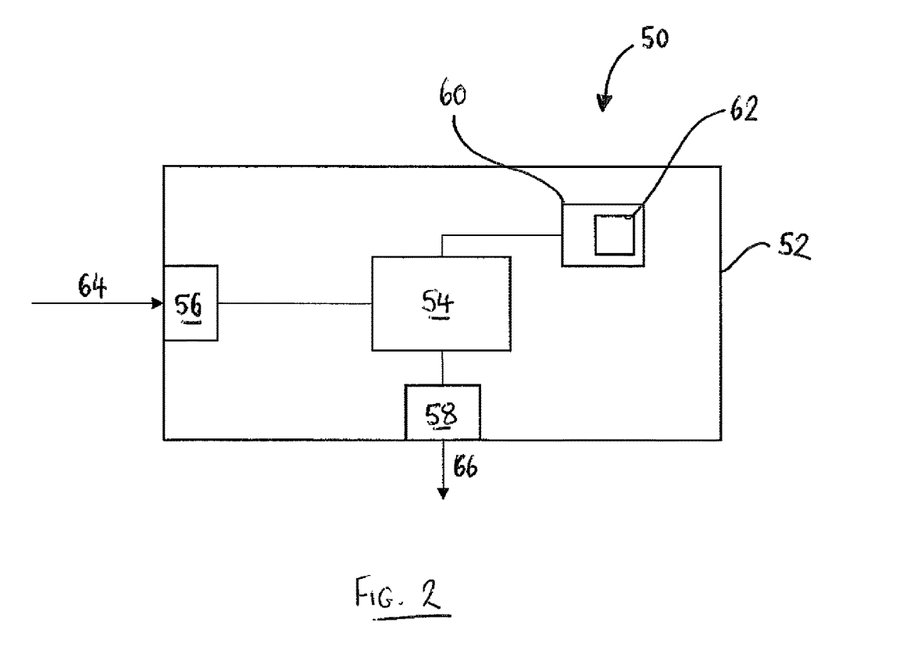
FIG. 2 is a schematic representation of an embodiment of a control system.

FIG. 2 illustrates an embodiment of a control system 50 in accordance with the invention.

The control system 50 includes a controller 52 having a processor 54. The processor 54 is operably coupled to an electrical input 56 for receiving an input signal 64. In use, the input signal 64 comprises data indicative of a measurement of condition(s) indicative of a hermeticity of the seal between the wound dressing 10 and the periphery of an associated wound site. The input signal 64 is received directly or indirectly (e.g. via a separate controller) from the plurality of sensors 16 in the wound dressing 10.

Figure 3:
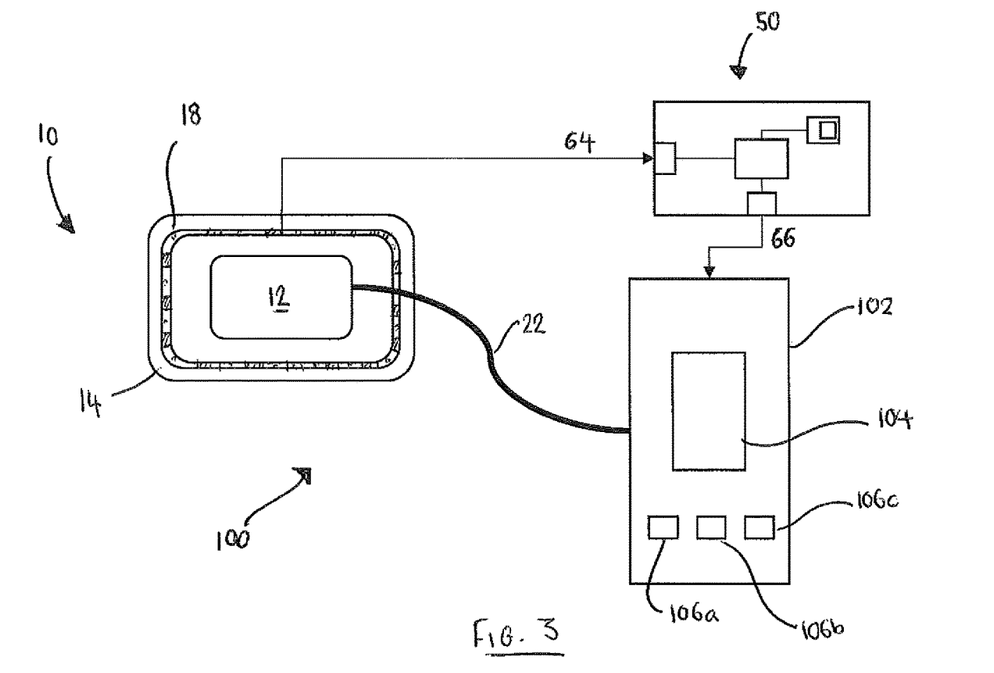
FIG. 3 is a schematic representation of an embodiment of a wound therapy apparatus.

The controller 52 includes a memory device 60 electrically coupled to the processor 54 and includes instructions 62 stored therein. The instructions 62 relate to operating instructions for controlling operation of a pressure gradient wound therapy apparatus 100 (FIG. 3). In use, the processor 54 is configured to access the memory device 60 and execute the instructions 62 in order to generate a control signal 66 for controlling operation of the wound therapy apparatus 100. The control signal 66 is output via electrical output 58.

As discussed, the controller 52 is configured to receive the input signal 64 from the plurality of sensors 16 within the wound dressing 10. The processor 54 is configured to analyse the input signal 64 to determine the hermeticity of the seal between the wound dressing and the periphery of the wound site. Specifically, the processor 54 may compare the values of condition(s) with one or more thresholds, or using a look-up table and determine the hermeticity in the region of each sensor 16 in dependence on such a comparison. In the illustrated embodiment, the processor 54 is configured to compare the pressure measurements obtained by the sensors 16 at a given time with an average pressure value of the sensed pressures at each of the plurality of sensors 16. An average pressure value may advantageously account for variations in the pressure associated with the seal between the adhesive region and the user's skin due to use factors, which may include a user leaning on the dressing, atmospheric pressure variations and pressure applied due to clothing worn by the user, for example. The processor 54 is configured to compare the pressure measurements obtained with the average pressure value and determine the presence of a leak/region of reduced hermeticity in dependence on measured pressure for a given sensor 16 differing from the average value by a given amount.

The processor 54 then generates and outputs the control signal 66 based on the determined hermeticity to control operation of the apparatus 100, for instance to provide an indication to the user of an area reduced hermeticity using indicators 20 (or indicators 106a, 106b, 106c—FIG. 3) and/or to control an operating characteristic of a pump assembly 102 (FIG. 3).

FIG. 3 illustrates an embodiment of a wound therapy apparatus 100 in accordance with the invention. The wound therapy apparatus 100 includes the wound dressing 10, control system 50 and a pump assembly 102. The pump assembly 102 may be of the type available from ConvaTec Ltd. under the Avelle trade mark.

As shown, wound dressing 10 is fluidly connected to a pump 104 of the pump assembly 102 via the conduit 22 which may likewise be of the type available from ConvaTec Ltd. under the Avelle trade mark. For positive pressure wound therapy, the pump 104 is configured to provide a source of air or other gas to be supplied to the interior portion of the wound dressing 10 to thereby increase the pressure within the wound dressing 10 relative to the surrounding environment. For negative pressure wound therapy, the pump 104 is configured to withdraw air from the interior portion of the wound dressing 10 to reduce the pressure within the wound dressing 10 relative to the surrounding environment.

The pump assembly 102 additionally includes indicators 106a, 106b, 106c consisting of lights which may be illuminated in dependence on the operational state of the pump 102 or indeed under instruction from the control system 50.

The apparatus 100 is controllable via control system 50.

Specifically, electrical input 56 of the controller 52 is operatively coupled to the plurality of sensors 16 associated with the wound dressing 10. As discussed herein, the input signal 64 received from the plurality of sensors 16 comprises data indicative of a measurement of one or more conditions indicative of the hermeticity of the seal between the wound dressing and the periphery of the wound site in the region of each sensor 16.

As discussed above, the processor 54 is configured to analyse the input signal 64 to determine to determine the hermeticity of the seal between the wound dressing and the periphery of the wound site. From this, the processor 54 is configured to generate and output the control signal 66 to the pump assembly 102 to control operation of the pump assembly 102 in accordance with one or more predetermined actions. For instance, the processor 54 can output a control signal 66 to control an operating characteristic of the pump 104—e.g. to moderate its power output or a speed of a motor associated with the pump 104—or to prevent further operation of the pump 104. Additionally or alternatively, the processor 54 can output the control signal 66 to the pump assembly 102 to control operation of the indicators 106*a*, 106*b*, 106*c* to indicate to the user a reduced hermeticity and/or of the operating state of the pump 104.

The control signal 66 in this embodiment is additionally output to the indicators 20 of the wound dressing, specifically to one or more indicators 20 proximal to a location of reduced hermeticity as determined based on the one or more conditions monitored by the sensors 16 adjacent to the one or more indicators 20.

Although shown separate in FIG. 3, it will be appreciated that in some embodiments two or more of the control system 50, wound dressing 10 and pump assembly 102 may be provided as a single unit, e.g. with the control system 50 and/or pump assembly 102 integrated within the wound dressing 10.

Figure 4:
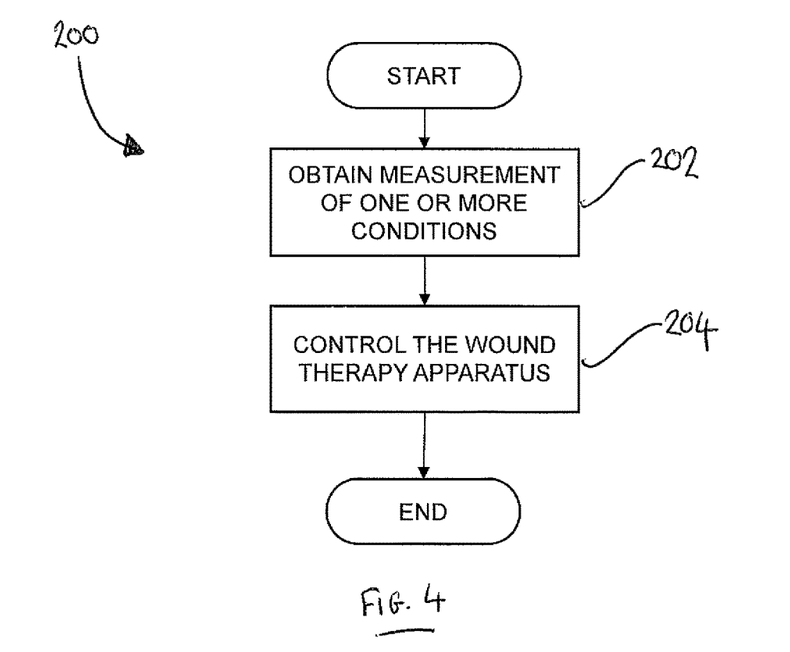
FIG. 4 is a flowchart illustrating an embodiment of a method in accordance with the invention.

FIG. 4 illustrates an embodiment of a method 200 in accordance with the invention, specifically for monitoring and controlling operation of the wound therapy apparatus 100.

At step 202, a measurement is obtained of one or more conditions indicative of a hermeticity of the seal between the wound dressing and the periphery of the wound site. The measurement is obtained using the plurality of sensors 16. A hermeticity of the seal between the wound dressing and the periphery of the wound site is determined based on these measurements.

Specifically, the method 200 comprises (at step 202) obtaining pressure measurements from the plurality of sensors 16 within the wound dressing 10. The measurements are analysed to determine the hermeticity of the seal between the wound dressing and the periphery of the wound site. Specifically, the method 200 comprises comparing the pressure measurements obtained by the sensors 16 at a given time with an average pressure value of the sensed pressures at each of the plurality of sensors 16. As discussed herein, an average pressure value may advantageously account for variations in the pressure associated with the seal between the adhesive region and the user's skin due to use factors. The method 200 comprises comparing the pressure measurements obtained with the average pressure value and determining the presence of a leak/region of reduced hermeticity in dependence on measured pressure for a given sensor 16 differing from the average value by a given amount. Where the pressure measurements at each sensor 16 are equal to (or within a given range from) the average pressure value it is determined that there is no area/region of reduced hermeticity—i.e. there is no leak.

At step 204, the method 200 comprises controlling operation of the pressure gradient wound therapy apparatus 100 in dependence on the determined hermeticity. This may include controlling indicators 20, indicators 106*a*, 106*b*, 106*c*, controlling the pump 104 of the pump assembly 102, and/or outputting a signal to a remote device as described herein. Where it is determined that there is no leak, the method may comprise taking no action at step 204, or controlling an indicator 106*a*, 406*b*, 106*c* to indicate this to the user.

Controlling the indicators 20, 106*a*, 106*b*, 106*c*, comprises controlling operation of those indicators 20, 106*a*, 106*b*, 106*c* to indicate to a user a reduction in hermeticity between the wound dressing and the user's skin, or to convey information regarding operation of the pump assembly 102—e.g. on, off, restricted, etc. The indicators (LEDs) 20 are used to indicate the location of an area of reduced hermeticity about the wound site. The indicators 106*a*, 106*b*, 106*c* are used to indicate an overall reduction in hermeticity and/or operation of the pump assembly 102 as described herein.

Controlling the pump 104 comprises controlling a power output or motor speed of the pump 104, e.g. activating the pump 104 in response to a reduced hermeticity between the wound dressing and the periphery of the wound site and/or increasing the power output/motor speed of the pump assembly in response to a reduced hermeticity between the wound dressing and the periphery of the wound site. Further, the pump 104 can be disabled in response to a reduced hermeticity between the wound dressing 10 and the periphery of the wound site.

In a variant, the sensors 16 may comprise resistive sensors which include a moveable or deflectable sensing element. An increase or decrease in pressure applied to such sensors may thereby be measured as a change in resistive values of one or more conductive elements of the resistive sensor(s) due to movement/distortion of the sensing element under the applied pressure. The pressure sensors may be a piezoresistive sensor, such as LPS22HH by STMicroelectronics.

The sensors 16 may additionally or alternatively comprise one or more temperature sensors; optical sensors; airflow sensors; and/or audio sensors each operable to measure a parameter indicative of the hermeticity of the seal between the adhesive region and the user's skin, e.g. in the manner described herein. Example temperature sensors include TO-92 by ST Microelectronics.

In a variant, the indicators 20, 106*a*, 106*b*, 106*c* may be replaced with an audio indicator (e.g. a speaker) for providing an audible indication to a user. For example, the audio indicators may be operable to output a warning alert or alarm in dependence on the one or more monitored conditions, e.g. in response to a reduction of hermeticity between the wound dressing 10 and the periphery of the wound site.

In a variant the control signal 66 may be output to a remote device such as a smartphone or the like. The control signal 66 may be output to the remote device for informing a user of the location of an area or region of reduced hermeticity between the wound dressing and the periphery of the wound site. For example, the remote device can include a display for presenting information to a user concerning the location of an area or region of reduced hermeticity between the wound dressing 10 and the periphery of the wound site. The remote device can, for example, be configured to present an image of the wound dressing. The image can include indicia at locations of the image of the wound dressing. The wound dressing 10 itself may include corresponding indicia thereon such that the image on the display of the remote device may be correlated with the wound dressing 10. For example, one or more regions on the image provided on the display of the remoted device, such as the relevant indicia may be highlighted in the image to inform the user of a location of an area or region of reduced hermeticity between the wound dressing 10 and the periphery of the wound site.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Each of the documents referred to above is incorporated herein by reference. Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, by-products, derivatives, and other such materials which are normally understood to be present in the commercial grade. The one or more embodiments are described above by way of example only. Many variations are possible without departing from the scope of protection afforded by the appended claims.

The invention claimed is:

1. A wound dressing for pressure gradient wound therapy, the wound dressing comprising:
    a dressing body configured to absorb exudate from a wound site; and
    an adhesive layer comprising an adhesive region for providing a seal between the wound dressing and a periphery of the wound site, the adhesive layer surrounding a periphery of the dressing body;
    wherein the adhesive layer further comprises a plurality of sensors associated with the adhesive region, configured to monitor one or more conditions indicative of a hermeticity of the seal between the wound dressing and the periphery of the wound site;
    wherein the plurality of sensors are distributed about the periphery of the dressing body; and
    wherein each of the plurality of sensors are embedded within the adhesive region and configured to identify a pressure associated with the seal between the adhesive region and the periphery of the wound site for each of the plurality of sensors.

2. A wound dressing as claimed in claim 1, wherein one or more sensors of the plurality of sensors comprise a micro-electromechanical system (MEMS) sensor or a nano-electromechanical system (NEMS) sensor.

3. A wound dressing as claimed in claim 1, wherein the plurality of sensors is arranged in a strip that at least partially surrounds the periphery of the dressing body.

4. A wound dressing as claimed in claim 1, wherein the plurality of sensors comprise a pressure sensor, operable to obtain a measurement indicative of a pressure associated with the seal between the adhesive region and the periphery of the wound site.

5. A wound dressing as claimed in claim 4, wherein the pressure associated with the seal between the adhesive region and the periphery of the wound site comprises an average pressure value determined by two or more pressure sensors.

6. A wound dressing as claimed in claim 1, wherein one or more sensors of the plurality of sensors comprise a temperature sensor, operable to obtain a measurement of a temperature gradient associated within the wound dressing.

7. A wound dressing as claimed in claim 1, wherein one or more sensors of the plurality of sensors comprise an optical sensor, wherein a light intensity level or frequency content of light measured by the one or more optical sensors is indicative of a level of hermeticity between the wound dressing and the periphery of the wound site.

8. A wound dressing as claimed in claim 1, wherein one or more sensors of the plurality of sensors comprise an airflow sensor operable to determine a measurement indicative of a speed and/or direction of airflow.

9. A wound dressing as claimed in claim 1, wherein the plurality of sensors are operable to output one or more signals indicative of the one or more monitored conditions for determining the hermeticity of the seal between the wound dressing and the periphery of the wound site, wherein the one or more signals are output via either a wired or wireless connection with a controller, and wherein the controller is operable to determine the hermeticity of the seal between the wound dressing and the periphery of the wound site in dependence on the one or more signals received via such connection from the plurality of sensors.

10. A wound dressing for pressure gradient wound therapy, the wound dressing comprising:
    an adhesive layer comprising an adhesive region for providing a seal between the wound dressing and a periphery of a wound site, wherein the adhesive layer further comprises a plurality of sensors embedded within the adhesive region, configured to monitor one or more conditions indicative of a hermeticity of the seal between the wound dressing and the periphery of the wound site; and
    one or more indicators operable to provide an indication to a user of the wound dressing in dependence on the one or more conditions monitored by the one or more sensors; wherein the one or more indicators comprise one or more of a visual indicator and an audible indicator;
    wherein the plurality of sensors are distributed about the periphery of the dressing body and each of the plurality of sensors are configured to identify a pressure associated with the seal between the adhesive region and the periphery of the wound site for each of the plurality of sensors.

11. A wound dressing as claimed in claim 10, wherein the one or more indicators are configured to be positioned, in use, about the periphery of the wound site to provide an indication at, or proximal to, a location of an area of reduced hermeticity in dependence on the one or more conditions monitored by the one or more sensors.

12. A pressure gradient wound therapy apparatus, comprising the wound dressing of claim 1, and a pump assembly for providing a source of positive or negative pressure to the wound dressing, in use.

13. A pressure gradient wound therapy apparatus according to claim 12, further comprising a controller, wherein the plurality of sensors are operable to output a signal indicative of the one or more monitored conditions to the controller for determining the hermeticity of the seal between the wound dressing and the periphery of the wound site.

14. A pressure gradient wound therapy apparatus according to claim 13, wherein the plurality of sensors comprise an electrical output, the controller comprises an electrical input; and the controller is operable to determine the hermeticity of the seal between the wound dressing and the periphery of the wound site in response to a signal, or signals from the plurality of sensors.

15. A pressure gradient wound therapy apparatus according to claim 14, wherein the plurality of sensors are configured such that the signal indicative of the one or more monitored conditions is output via either a wired or wireless connection with the controller, the controller being operable to determine the hermeticity of the seal between the wound dressing and the periphery of the wound site in dependence on the signal or signals received via such connection from the plurality of sensors.

16. A control system for controlling operation of a pressure gradient wound therapy apparatus comprising a wound dressing for pressure gradient wound therapy, the wound dressing comprising: an adhesive layer comprising an adhesive region for providing a seal between the wound dressing and a periphery of a wound site; wherein the adhesive layer further comprises one or more sensors embedded within the adhesive region about the periphery of the wound dressing, configured to monitor one or more conditions indicative of a hermeticity of the seal between the wound dressing and the periphery of the wound site; and a pump assembly for providing a source of positive or negative pressure to the wound dressing, in use; the control system comprising one or more controllers, and being configured to:

receive an input signal from at least one sensor of the wound dressing indicative of the monitored one or more conditions;

output a control signal for controlling operation of the pressure gradient wound therapy apparatus in dependence on the one or more conditions; and determine a hermeticity of the seal between the wound dressing and the periphery of the wound site in dependence on the one or more conditions.

17. A control system according to claim 16, which is configured to output a control signal for controlling operation of one or more indicators in dependence on the one or more conditions for providing an indication to a user of the wound dressing indicative of the hermeticity of the seal between the wound dressing and the periphery of the wound site; the control system being operable to output a control signal to one or more indicators provided at, or proximal to, a location of an area of reduced hermeticity to direct a user to the location of an area or region of reduced hermeticity between the wound dressing and the periphery of the wound site; the location corresponding to a specific area or region of the seal provided between the wound dressing and the user's skin about the periphery of the wound site.

18. The control system of claim 16, wherein the control system is further configured to receive at least one additional input signal from at least one additional sensor of the wound dressing, and to determine a location of a leak in the seal based upon the input signal and the at least one additional input signal.

19. The wound dressing of claim 1, further comprising a plurality of indicators, wherein the plurality of indicators are distributed about the periphery of the dressing body.

20. The wound dressing of claim 1, wherein the plurality of sensors comprise at least one capacitive sensors having a moveable sensing element capacitively coupled and moveable with respect to an electrode.

21. The wound dressing of claim 10, wherein the one or more indicators are located in the adhesive region.

* * * * *